United States Patent [19]

Hutt

[11] Patent Number: 5,042,930

[45] Date of Patent: Aug. 27, 1991

[54] OPTICAL SYSTEM WHICH ALLOWS COINCIDENT VIEWING, ILLUMINATING AND PHOTOGRAPHING

[75] Inventor: Marvin K. Hutt, Oakland, N.J.

[73] Assignee: Luxtec Corporation, Sturbridge, Mass.

[21] Appl. No.: 419,896

[22] Filed: Oct. 11, 1989

[51] Int. Cl.$^5$ .............................................. G02B 23/02
[52] U.S. Cl. .................................. 359/375; 359/407; 359/389
[58] Field of Search ............... 350/545, 145, 146, 399, 350/524, 514, 170, 400, 403; 351/158

[56] References Cited

U.S. PATENT DOCUMENTS

| | | | |
|---|---|---|---|
| 2,111,187 | 3/1938 | Keeler | 88/20 |
| 2,246,817 | 6/1941 | Sauer | 88/23 |
| 2,318,705 | 5/1943 | Morgan | 350/399 |
| 3,066,569 | 12/1962 | MacDonald | 88/1 |
| 3,853,398 | 12/1974 | Kano | 350/524 |
| 4,448,498 | 5/1984 | Muller et al. | 350/447 |
| 4,516,190 | 5/1985 | Kloots | 362/32 |
| 4,593,683 | 6/1986 | Blaha | 128/23 |
| 4,759,615 | 7/1988 | Bainbridge et al. | 350/399 |
| 4,834,525 | 5/1989 | Vansaghi | 351/158 |

OTHER PUBLICATIONS

Smith, "Prisms and Mirrors", Modern Optical Engineering, 1980, pp. 92–95.
American Journal of Ophthalmology, May 1971, advertisement by the Xonix Corp.

Primary Examiner—Bruce Y. Arnold
Assistant Examiner—James Phan
Attorney, Agent, or Firm—Weingarten, Schurgin, Gagnebin & Hayes

[57] ABSTRACT

A binocular surgical loupe which enhances the illumination of the viewed field while avoiding flare effects of illuminating light within the loupe optics. The binocular system utilizes circularly polarized illumination and viewing to prevent flare effects and additionally enhances the illumination of the field of view by utilization of the illumination source waste beam that results from the presence of a beam splitter in the illumination path within the loupe. In addition, a camera system is provided which permits remote viewing of the user's field of view. In one embodiment the camera and view paths include separate, identical zoom lenses which are synchronously controlled so that the fields of illumination and view are kept coextensive. In another embodiment for a binocular loupe, the loupe optics for one eye combines illumination and viewing functions while the loupe for the other eye combines camera and viewing functions.

9 Claims, 3 Drawing Sheets

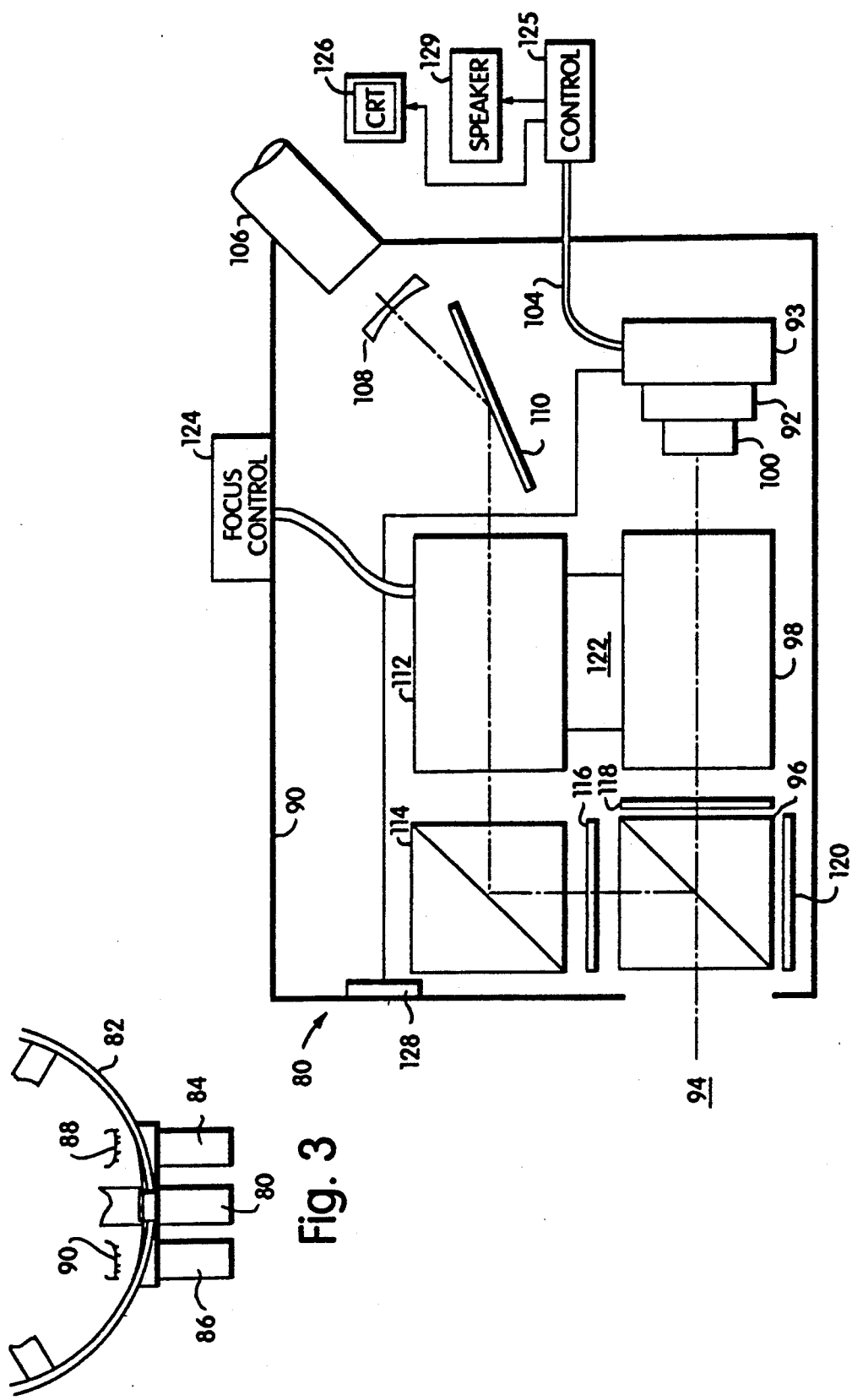

OPTICAL SYSTEM WHICH ALLOWS COINCIDENT VIEWING, ILLUMINATING AND PHOTOGRAPHING

FIELD AND BACKGROUND OF THE INVENTION

The present invention relates to optical loupes utilized in surgical and other procedures for providing magnified viewing and illumination of fields of interest to a surgeon or other user. Such systems typically include first and second loupes which permit binocular viewing with magnification of a region of interest. Illumination has been Provided in the past by a separate illumination source, typically located and supported in the forehead region of the surgeon More recently, and as represented in co-pending U.S. Application Ser. No. 07/327,644, filed March 23, 1989 now abandoned, the illumination function is combined into the viewing loupe in order to avoid the shadow cast in the field of view by a light source located away from the viewing axis. In such combined optics it is important to prevent the high intensity illumination, passing through the loupe from the illumination source, from creating a flare effect, typically from a brightness at the interface of the loupe beam splitting optics.

At the same time, because of the attenuation in loupe beam splitter optics, some illumination is lost both in the path of illumination from the source and in the path of viewing by the operator of the field of view. It is important that the optics minimize attenuation and maximize the perceived illumination of the field of view while avoiding flare effects.

It is additionally desirable to provide a video image of the user's field of view to provide offsite display and control of that field of view without interfering with the user's procedures or views.

BRIEF SUMMARY OF THE INVENTION

In accordance with the teaching of the Present invention a binocular loupe system is provided for surgical or related usages. The loupe system provides illumination of the field of view along the viewing axis and includes optics which enhance the illumination and brilliance of the field of view while minimizing the effects of flare resulting from the presence of intense illuminating radiation passing through the optics which also lie in the view path of the loupe. Additional embodiments provide video viewing of the field of view and remote presentation of the image along with synchronized remote control of illumination and viewing optics for the view scene. In an alternative embodiment a video viewing system is integrated into a viewing loupe of a binocular loupe system while the other loupe provides on axis illumination in combination with operator viewing.

BRIEF DESCRIPTION OF THE DRAWING

These and other features of the present invention are more fully set forth below in the solely exemplary detailed description and accompanying drawing of which:

FIG. 3 is a diagrammatic view of a video camera system in use alongside a binocular loupe;

FIG. 4 is an internal view of the video camera system of FIG. 3;

DETAILED DESCRIPTION

The present invention contemplates a surgical loupe system in which the optical design provides for enhanced brilliance in the operator's view and provides a video output of the field of view of the operator.

Figure 1:
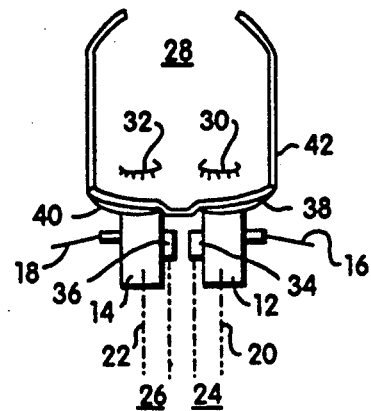
FIG. 1 is a diagrammatic view of a binocular loupe system according to the present invention.

In accordance with one embodiment of the invention in FIG. 1, a binocular viewing system comprises first and second loupes 12 and 14. Illumination is delivered through optical fibers 16 and 18 for each loupe 12 and 14. Optics within the loupes 12 and 14 direct the illumination provided by the fibers 16 and 18 along respective output axis 20 and 22 to illuminate respective fields of view 24 and 26. The fields of view 24 and 26 will coincide at the normal operator viewing distance. An operator 28 views the fields of view 24 and 26 through respective eyes 30 and 32 aligned to view along the axes 20 and 22 through loupes 12 and 14. Illumination provided from the fibers 16 and 18, which would otherwise be waste illumination, is captured by the loupe optics and directed towards the respective fields of view 24 and 26 by optical subassemblies 34 and 36. The loupes 12 and 14 and associated optics illustrated in FIG. 1 are substantially identical and are mounted for ease of operator use either on a separate headband or, as illustrated in FIG. 1, directly in lenses 38 and 40 of a pair of eyeglasses set in a frame 42 and custom adapted to the surgeon's needs. In so customizing the eyeglasses, the loupes 12 and 14 are fitted into the glass lenses 38 and 40, typically by screwing them into apertures formed in the lenses in locations custom designed to match the viewing direction of the surgeon's eyes 30 and 32 while permitting peripheral viewing by the surgeon through the lenses 38 and 40 by moving his eyes.

Figure 2:
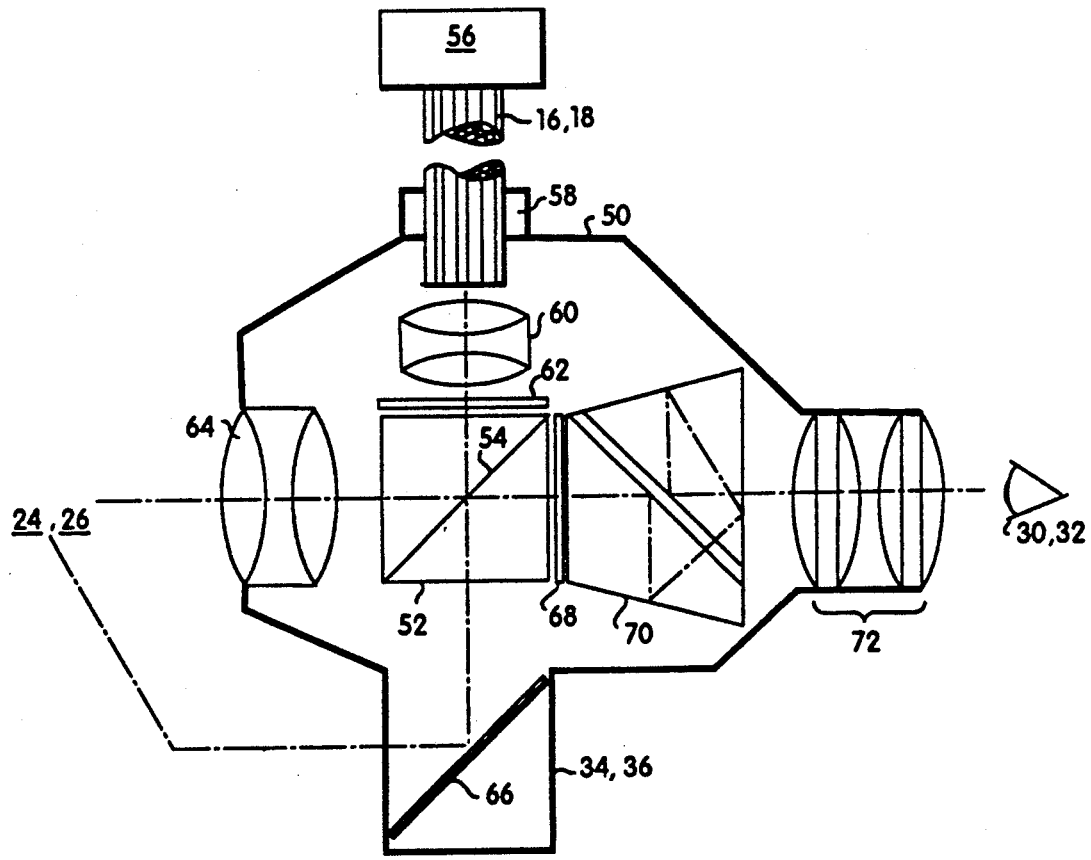
FIG. 2 is an internal view of a representative loupe of the binocular loupe system of FIG. 1.

The loupes 12 and 14 are substantially identical although they may be provided in right and left hand forms. FIG. 2 illustrates the internal structure of each loupe 12 and 14. As shown there a housing 50 is provided with a beam splitting optical cube 52 with a beam splitting interface 54 mounted within the housing 50. The beam splitting interface 54 preferably provides 50% reflection and 50% transmission which provides optimal scene and viewing brightness.

The optical fibers 16 or 18 which supply illumination from a source 56 are mounted through a support 58 to the housing 50 to direct illumination through a lens system 60 and circular polarizing filter 62 for reflection from a first surface of the beam splitting interface 54 outward through a further, objective lens system 64 to illuminate the field of view 24 or 26. That portion of the radiation, typically 50%, which passes through the beam splitting interface 54 extends onward through the housing 50 to a reflector 66 within the subassemblies 34 or 36 from which it is directed generally to illuminate the field of view 24 or 26 at the location where the surgeon or other operator is to view it.

Rays from the illuminated image returning from the field of view 24, 26 pass back through lens 64 to optical interface 54 where it is transmitted, in part, through the first to the second surface of the interface 54 to a circular polarizing filter 68 and a Pechan/Schmidt roof prism 70 on through eyepiece optics 72 to an eye 30, 32 of the viewer.

The polarizing filters 62 and 68 provide circular polarization which attenuates the radiation only by 20% while transmitting 80%. The dimensions of the path between the polarizing filters 62 and 68 for light which causes perceivable brightness or flare at the interface 54 within the cube 52 is such that all such illumination is attenuated by the combined polarizations of the filters 62 and 68. Scattering by objects within the field of view 24, 26, however, causes the returning illumination to loose a defined polarization such that the filter 68 is relatively ineffective in attenuating that illumination which in turn passes through the optics 70 and 72 to the viewing eye 30, 32.

The Prism 70, provides an erratic image and further lengthens the optical path in order to achieve a desired focal length for the telescope formed by objective lens system 64 in combination with eyepiece lenses 72. The lens system 60 is provided in order to optimize the available illumination from the optical fiber 16, 18 so that it illuminates the same field of view 24, 26, or portion thereof, as seen by the viewer's eye 30, 32.

It is desirable in many applications to provide a remote image of the field of view observed by the surgeon or other operator during whatever procedure the surgeon or operator is engaged in. Such viewing can be for purposes of remote monitoring by assisting personnel or for use in teaching. It may also be useful for providing video recording of procedures. For such purposes, according to the present invention, an optical camera system 80, as illustrated in FIG. 3, is attached to a headband 82 of the type known in the art and securely fitted about the head of the operator in such position that it typically lies between loupes 84 and 86 which are positioned, either by eyeglass supports or additionally supported by the headband 82, to permit the operator's eyes 88 and 90 to view respectively therethrough. Loupes 84, 86 may be of the design described above, other design, or may be omitted entirely.

The structure of the camera system 80 is illustrated more fully below with respect to FIG. 4. As shown there the camera 80 includes a housing 90 having therein a charge couple device (CCD), video sensor chip 92 and amplifier/driver pc board 93. Chip 92 responds to the light from a field of view 94 after passing through a beam splitter 96, zoom lens 98 and infrared filter 100 to provide a corresponding video signal that is amplified on the board 93 to drive an output cable 104 to a controller 125 and monitor 126 or other utilization device.

The field of view 94 is illuminated by light from an optical fiber 106 through a lens 108 and reflector 110 which positions the illumination to pass through a zoom lens 112 to be reflected by a reflector 114 from which it is reflected off the beam splitter 96 to travel the same optical axis as viewed by the chip 92 toward the field of view 94. Polarizing filters 116 and 118 may be provided as described above with respect to FIG. 2 in the path of illumination from the cable 106 and in the viewing path after passing through the beam splitter 96 in order to eliminate from the image processed by the chip 92 all flare from the beam splitter 96 resulting from its illumination by light from the cable 106. An absorber 120 may additionally be provided so that all radiation passing through the beam splitter 96 from the illuminating light in cable 106 is absorbed and not permitted to reflect within the housing 90 causing further undesirable optical or flare effects. A subassembly such as described above may alternatively be provided to make use of this waste beam.

The zoom lenses 98 and 112 are typically identical and are coupled either mechanically or electrically by a coupling 122 to vary their focal lengths together. A focus control 124 is provided remotely, typically at the location of viewing monitor 126 for the video image transmitted by the processor chip 92. The use of coordinated zoom lenses 98 and 112 permits the region of illumination to track in size the region of view seen by the video sensor chip 92. This in turn provides optimal utilization of the incident illumination.

A microphone 128 is mounted on a suitable surface of the housing 80, such as on the front as shown, and its output is coupled into the cable 104 through the amplifier/driver board 93. The audio discussions during the operation or procedure are thus remotely transmitted to controller 125 where they are reproduced by a speaker 129.

Figure 5:
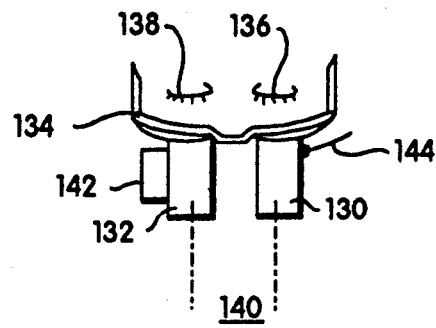
FIG. 5 is a diagrammatic view of a binocular loupe system having integrated into one loupe a video camera system.
Figure 6:
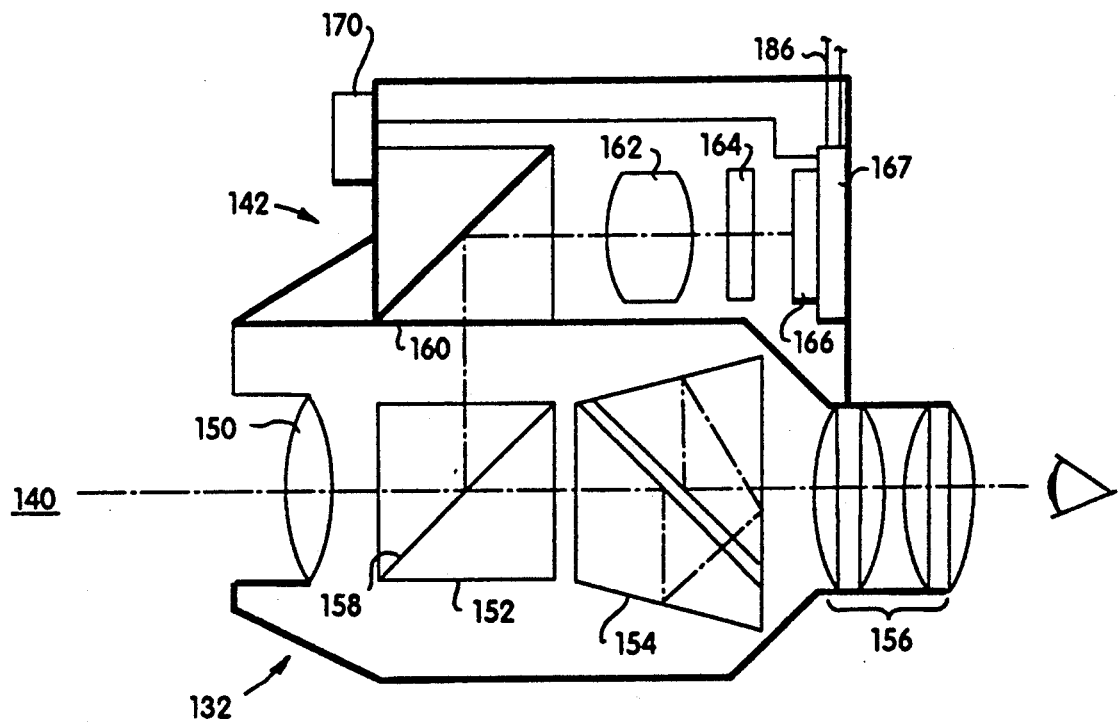
FIG. 6 is an internal view of the loupe and associated camera system of FIG. 5.

Alternatively, a video camera may be incorporated into a binocular loupe system as illustrated in FIGS. 5 and 6. As shown in FIG. 5 first and second loupes 130 and 132 are provided and supported by a means 134 which may include either eyeglass lenses and/or frames or a separate headband as desired. The loupes 130 and 132 are positioned, as described above, in coordination with the operator's eyes 136 and 138 to permit optimal viewing of a field of view 140. One of the loupes, shown here as loupe 132, has associated with it a video camera 142 the design of which, and the associated loupe 132, are more fully described below in FIG. 6. The other loupe 130 typically is of the design illustrated above in FIG. 2 with or without a waste beam utilization subassembly 34, 36 and is supplied with illumination from an optical fiber 144. As thus shown both loupes 130 and 132 provide viewing by the operator of the field of view 140. The loupe 130 is additionally constructed to provide illumination along the same axis as is used for viewing while the loupe 132 is constructed to provide video sensing of the image along the same axis as used for viewing.

With respect to FIG. 6 the details of the loupe 132 and associated camera 142 are more fully described. As shown there, viewing of the field of view 140 is accomplished along an optical axis which passes through an objective lens 150, beam splitter 152, Pechan/Schmidt prism 154 and objective lens 156. The beam splitter 152 has a beam splitting interface 158 which provides an appropriate percentage of transmission and reflection depending upon the sensitivity of the video camera and the matching transmission of the companion loupe 130. Typical transmission reflection percentages would be 50/50. The light reflected by the beam splitting interface 158 is directed upwards where a reflector 160 redirects it within the video camera portion 142 through an optical system 162 and infrared filter 164 to a video sensor chip 166, also typically a charge coupled device (CCD), to an amplifier/driver 167. The video sensor 166 converts the received image to a video signal which is applied as an output on a cable 168 by amplifier/driver 167 to a video monitor or otherwise as desired. A front mounted microphone 170 is also provided and its output is applied through amplifier/driver 167 to the cable 168.

In this manner the structure of FIGS. 5 and 6 provides both on axis viewing as well as video photography through a single pair of binocular loupes 130 and 132.

It is to be noted that for weight minimization in the optical designs above plastic lenses are typically utilized along with other lightweight materials. Specific structures for embodying the structure and concepts illustrated above, or different combinations of them are considered to be within the scope of the invention which is solely limited in accordance with the following claims.

I claim:

1. A viewing loupe comprising:
   a housing;
   beam splitter means supported within said housing for receiving on a first axis at a first beam splitter surface an illumination and for reflecting said illumination toward a field of view;
   first means for providing circular polarization in the illumination applied to said first surface;
   a path lengthening prism placed along a second axis substantially angled to the first axis of said illumination and positioned within said housing to receive an illumination from said field of view passing through said beam splitter means from said first to a second surface;
   second means for providing circular polarization along said second axis of said operator viewing optics and positioned to attenuate brightness in said beam splitter means resulting from said illumination passing therethrough.

2. The loupe of claim 1 wherein said beam splitter means provides 50/50 beam splitting.

3. The loupe of claim 1 wherein said beam splitter means is an interior surface of an optical cube.

4. The loupe of claim 1 wherein said prism includes a Pechan/Schmidt prism.

5. A binocular loupe comprising:
   a housing having viewing optics for each eye of an operator wherein each said viewing optics comprise the loupe of claims 1, 2, 3, or 4.

6. The binocular viewing system of claim 5 further including means for supporting said loupes in position for operator viewing therethrough.

7. The system of claim 6 wherein said supporting means includes:
   an eyeglass frame and lenses; and
   means for mounting said loupes in the lenses of said eyeglass frame.

8. A viewing loupe comprising:
   a housing;
   beam splitter means supported within said housing for receiving on a first axis at a first beam splitter surface an illumination and for reflecting said illumination toward a field of view;
   first means for providing circular polarization in the illumination applied to said first surface;
   operator viewing optics placed along a second axis substantially angled to the first axis of said illumination and positioned within said housing to receive an illumination from said field of view passing through said beam splitter means from said first to a second surface, said operator viewing optics including a path lengthening prism;
   second means for providing circular polarization along said second axis of said operator viewing optics and positioned to attenuate brightness in said beam splitter means resulting from said illumination passing therethrough.

9. The loupe of claim 8 wherein said path lengthening prism includes a Pechan/Schmidt prism.

* * * * *